US005787899A

United States Patent [19]

Culp

[11] Patent Number: 5,787,899

[45] Date of Patent: Aug. 4, 1998

[54] METHOD OF RELIEVING PAIN AND DISCOMFORT IN HUMAN BEINGS

[76] Inventor: Deborah Culp, 4105 W. Cullerton, Chicago, Ill. 60623

[21] Appl. No.: 681,086

[22] Filed: Jul. 22, 1996

[51] Int. Cl.[6] .............................. A61B 19/00

[52] U.S. Cl. .............................. 128/898; 600/27

[58] Field of Search .............................. 128/898, 897; 606/204; 131/270; 434/262; 600/26–27

[56] References Cited

PUBLICATIONS

Hare, Martha L. "Shiatsu acupressure in nursing practice" Holistic Nursing Practice 2(3):68–74, 1988.

Matsumura, Wynn M. "Use of acupressure techniques and concepts for nonsurgical management of TMJ disorders" Journal of General Orthodontics vol 4: 5–16, Mar. 1993.

*Primary Examiner*—Vincent Millin
*Assistant Examiner*—Kelly O'Hara
*Attorney, Agent, or Firm*—Hamman & Benn

[57] ABSTRACT

A method of treatment using applied manual pressure to certain key pressure points of the forearms of a human body, in order to relieve pain or discomfort brought on from illness. The method includes manually applying pressure by the hands of a therapist along the forearms of a patient, while the patient clasps his hands and extends his arms outwardly from the body, so as to form a substantially triangular arrangement, with his two arms serving as two legs of the triangular, and an imaginary line from the two elbows. The patient forcefully pushes his hands and arms toward each other while in the triangular arrangement, with such pushing being concentrated at the clasped hands, and specifically concentrated at the metacarpals, and in the chest, and specifically at the sternum. Thereafter, the therapist applies external pressure along the forearms of the patient, or specifically applying manual pressure along each interior forearm with a thumb along the brachioradialis muscles of the radius bone, while simultaneously applying pressure with one or more fingers along the exterior of the forearm along the extenson calpi ulnaris muscle of the ulna bones. The pressure is continuously applied along each forearm, until the elbow.

2 Claims, 4 Drawing Sheets

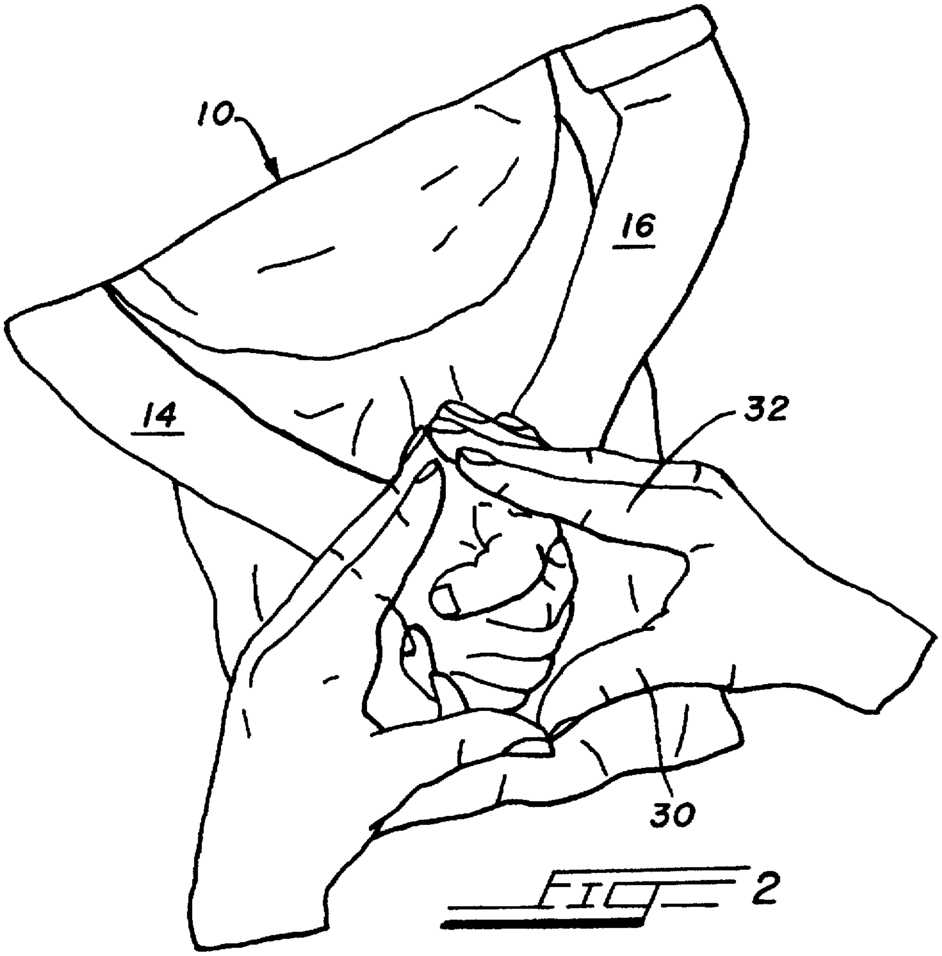
FIG. 2
FIG. 3
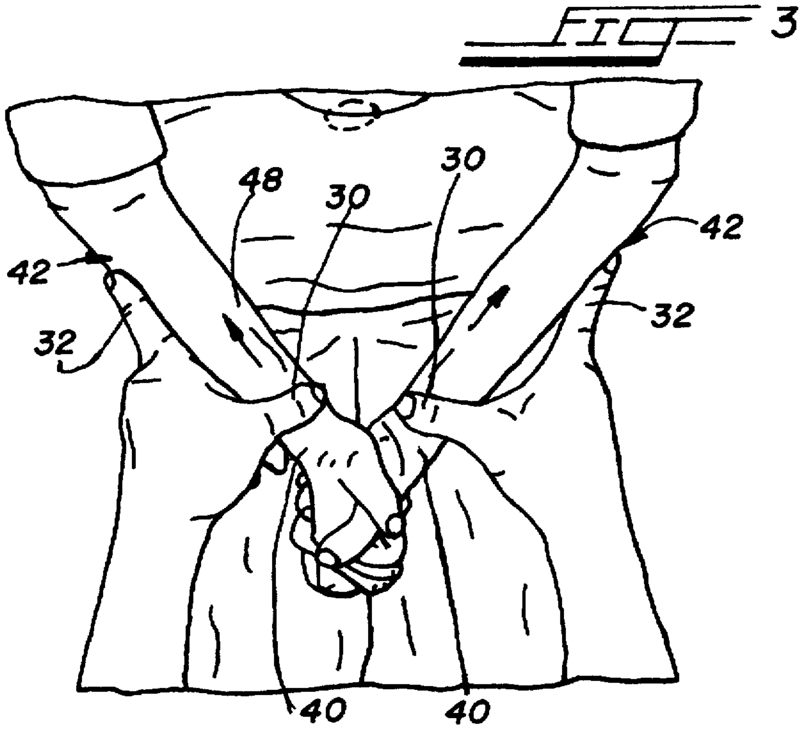

METHOD OF RELIEVING PAIN AND DISCOMFORT IN HUMAN BEINGS

BACKGROUND OF THE INVENTION

The present invention is directed to a treatment using applied manual pressure to certain key pressure points of the forearms of a human body, in order to relieve pain or discomfort brought on from disease or drug addiction. The present invention has been found efficacious, at least temporarily, in eliminating the symptoms of withdrawal associated with heroine addiction, and has, also, at least temporarily, eliminated all pain stemming from systemic disease or debilitating illnesses, such as migraine headaches or from psychological disturbance.

SUMMARY OF THE INVENTION

It is the primary objective of the present invention to provide a treatment for relieving pain and discomfort in human beings by manually applying pressure by hands to a patient along the forearms of the patient, while the patient clasps his hands and extends his arms outwardly from the body, so as to form a substantially triangular arrangement, with his two arms serving as two legs of the triangular, and an imaginary line from the two elbows, and specifically an imaginary line between the two capitulum bones, forming the third leg thereof.

It is another objective of the present invention to have the patient forcefully push his hands and arms toward each other while in the triangular arrangement, with such pushing being concentrated at the clasped hands, and specifically concentrated at the metacarpals, and in the chest, and specifically at the sternum.

It is another objective of the present invention for a therapist to apply external pressure along the forearms of the patient, or specifically applying manual pressure along each interior forearm with a thumb along the brachioradialis muscles of the radius bone, while simultaneously applying pressure with one or more fingers along the exterior of the forearm along the extenson calpi ulnaris muscle of the ulna bones. The pressure is continuously applied along each forearm, until the elbow, and specifically including the application of pressure with one or more fingers to the coronoid process, which controls articulation when the elbow is bent, and also to the olecranon process, which controls articulation when the elbow is extended.

BRIEF DESCRIPTION OF THE DRAWINGS

The invention will be more readily understood with reference to the accompanying drawing, wherein:

FIG. 2 is a front view thereof, showing the initial pressure treatment;

FIG. 3 is a top view thereof showing the actual pressure treatment along the forearms;

DETAILED DESCRIPTION OF THE INVENTION

Figure 1:
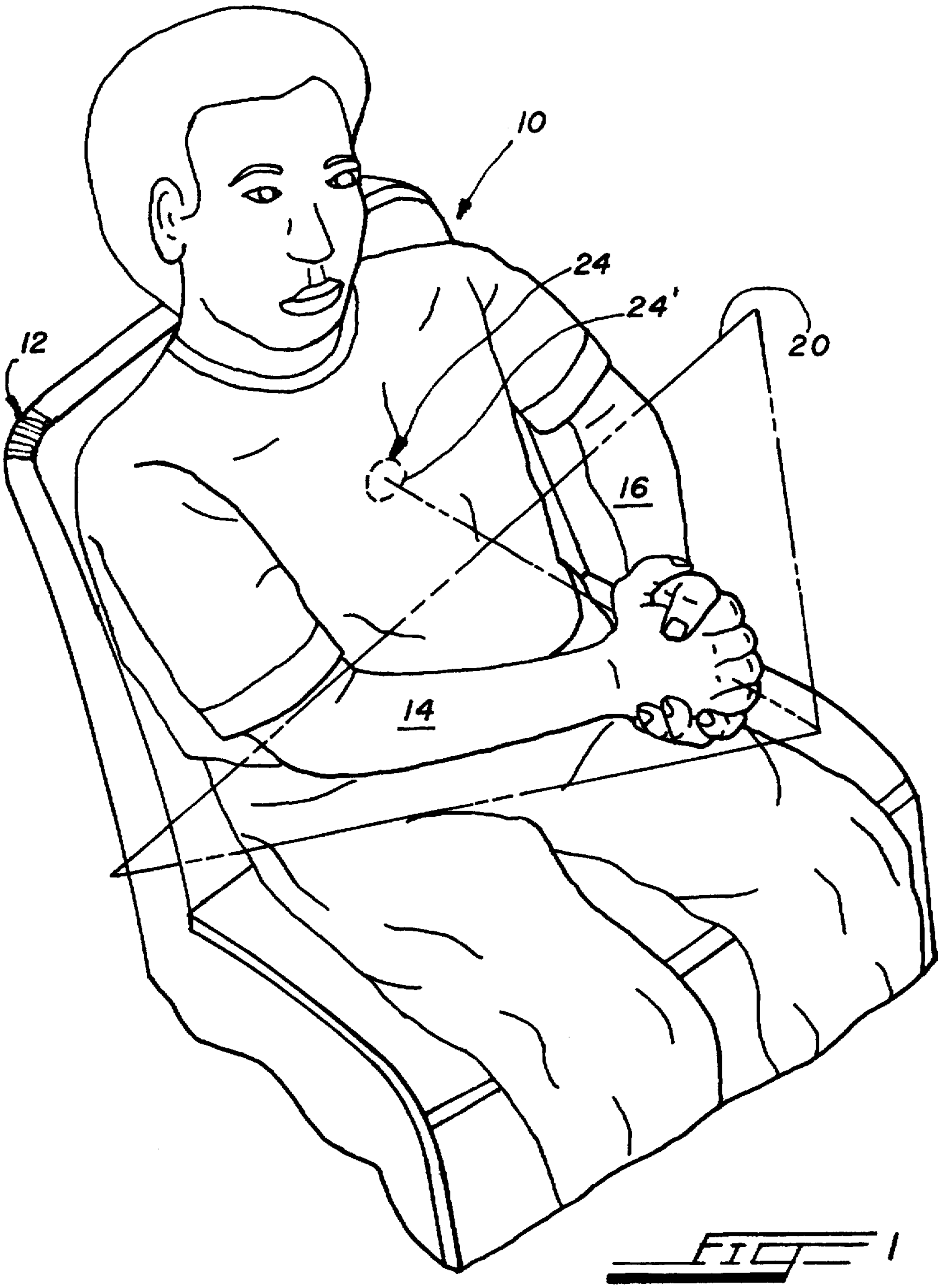
FIG. 1 is an isometric view showing the position that a patient must position his arms in order to form the necessary triangular arrangement thereof for receiving the pressure treatment of the invention.

Referring now to the drawings in greater detail, a patient 10, who is to be treated by the method of the invention, is seated in a chair 12, and made to relax. The patient is then instructed to extend his arms in front, and to clasp his hands in the manner depicted, where the left and right thumbs are crossed over each other, and the fingers of the left and right hands are crossed at right angles. It is critical that the patient form what may be called a "triangular arrangement", where the forearms 14, 16 form two legs of a triangle, and where the third leg of the triangle is an imaginary line 20 extending between the left and right elbows, and, specifically, a line joining the two coronoid process bones, which are part of the ulna bones facing exteriorly. It is, also important that the forearms, with the clenched hands, be held at an elevation approximately equal in height to the sternum 24, and, in particular, at the height of the xiphoid process bone 24', which is the bottom portion of the sternum. While the patient is in this position, as depicted in FIG. 1, he is instructed to apply pressure to the clenched hands, such that each hand and forearm is forced or pushed forcefully against each other, whereby pressure is applied not only at the clenched hands, but is also radiated along the entire muscles of the forearms. This pressure also causes pressure, or a force, to exist or be felt at the sternum bone region of the chest, or, more specifically, the xiphoid process bone adjunctive tissue 24', all of which is necessary for the treatment of the invention. It is the fact that the sternum is placed in compression that allows for the manually-applied pressure along the forearms by a trained medical therapist to be effective in relieving pain and discomfort.

Figure 4:
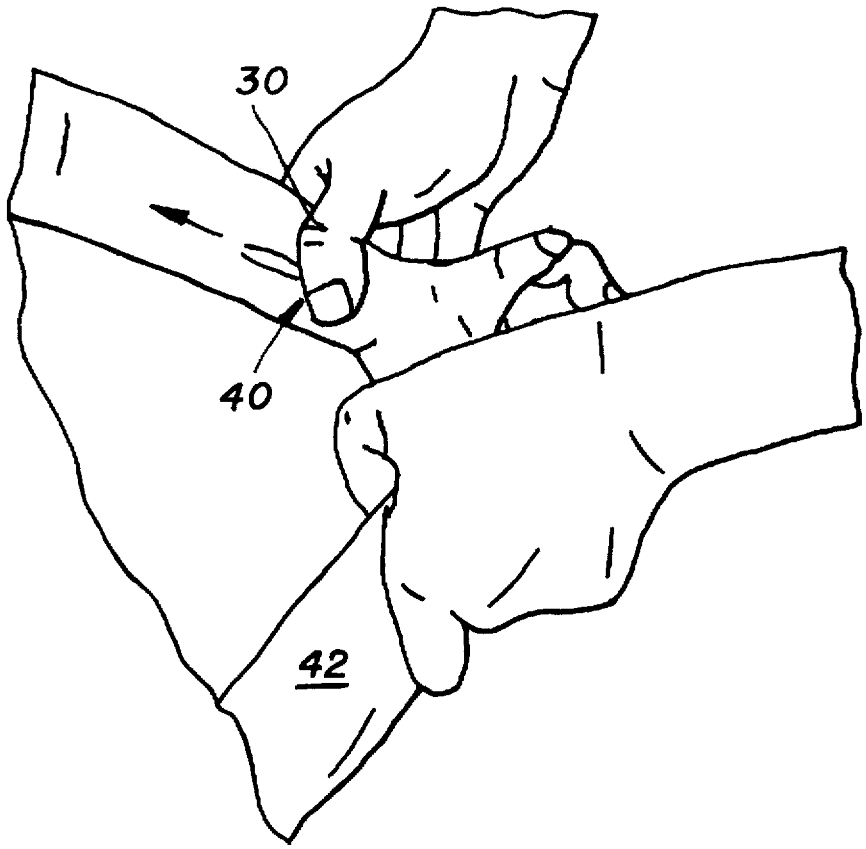
FIG. 4 is a detailed top view showing the positioning of the hands of the therapist administering the pressure treatment along the forearms.
Figure 5:
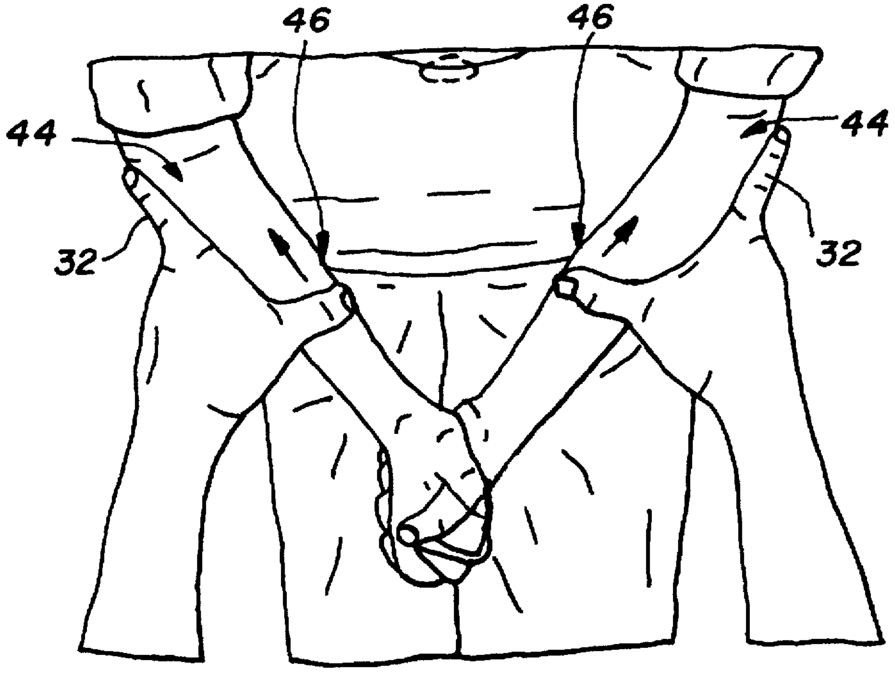
FIG. 5 is a top view showing the latter stages of the pressure treatment along the forearms.
Figure 6:
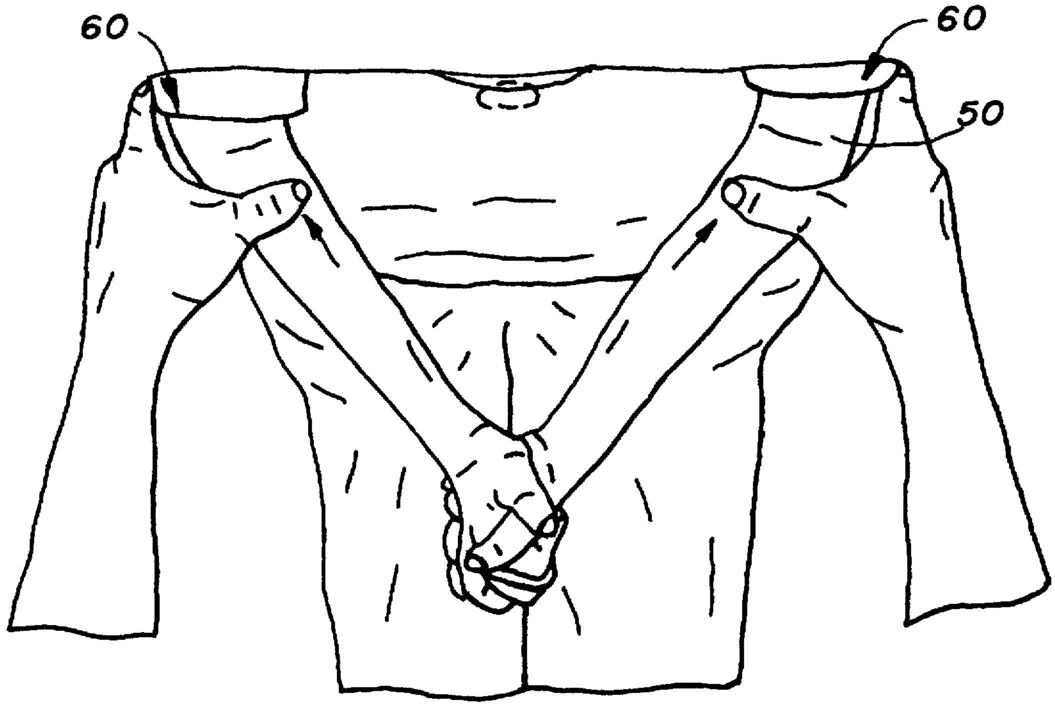
FIG. 6 is a top view showing the final stage of the pressure treatment at the elbows.

As soon as the medical therapist feels that the patient has successfully stressed the clenched hands, forearms, and sternum, he then begins the actual therapy. The actual therapy consists initially of placing the therapist's hands around the clenched hands of the patient, as seen in FIG. 2, in order to help calm the patient and as an indicator to ensure that the triangular arrangement is maintained. Then, the therapist starts the pressure applications along each forearm, as seen in FIGS. 3 and 4. The therapist initially holds his hands such the thumb 30 of each hand is located interiorly for applying considerable localized pressure thereby on the anterior extensor digitorum muscle area 40 closest to the wrist, while the forefinger 32 of each hand applies considerable localized pressure against the posterior extensor carpi ulnaris muscle area 42. This pressure may be applied for just a few seconds or longer, depending upon the therapist's opinion as to the state of the patient. Thereafter, the therapist gradually moves his hands upwardly along the forearms, toward the elbow. During this upward movement of the therapist's hands along the forearms, the hands of the therapist are gripped about the forearms as depicted in FIGS. 3–6. After having applied concentrated pressure near the wrist, as above-described, the therapist moves his hands upwardly to apply pressure to the rest of the posterior extensor carpi ulnaris muscle area 44 of each forearm via his forefingers, and to apply pressure to the anterior brachioradialis muscle area 46 of each forearm, via his thumbs, starting with the extensor carpi radialis bravis muscle area 48, up to the extensor carpi radialis longus 50 at the elbow, as the therapist's hands are moved ever-so slowly upwardly along the forearms or as guaged by transdermal feedback response. When the therapist's hands have reached the elbow, on the anterior side, pressure is applied to the flexor carpi ulnaris muscles 60 by means of the forefingers. Also, upon reaching the elbows, concentrated pressure is applied via the forefingers to the ulna coronoid process bones which articulates with the coronoid fossa of the humerus, or the upper arm, when the elbow is bent and also applies pressure to the olecranon process bone of the ulna which articulates with the olecranon fossa of the humerus, or the upper arm, when the elbow is extended. While these ulna bones of the elbow are being pressured, the thumbs of the hands continue to apply concentrated force to the remainder of the upper anterior brachioradialis muscles, the upper part of the extensor carpi radialis brevis. During the entire time interval that the therapist is applying concentrated, localized pressure to the forearms of the patient, the patient must continue to maintain the triangle position of his hands and forearm together forcefully, so that the "squeezing", or compressive forces are felt at the sternum and/or surrounding tissues as described above. The result from this treatment of the invention is felt almost immediately by the patient. This relief from pain, discomfort, addiction or from the need for dependency on drugs, has been found to last well after the treatment in the majority of cases. However, follow-up treatments may, occassionally, be necessary. Fallow up treatments if necessary are identical to the first treatment above-described, and may be scheduled twice or more a week, depending upon the failure of the first pressure treatment may warrant an alternative clinical intervention.

While the preferred embodiment has disclosed the application of pressure along the forearms by means of the hands of the therapist, it is contemplated to use pressure-creating apparatuses, such as massagers, and the like, for applying the pressure to the forearms in the manner above-described.

While specific embodiments of the invention have been shown and described, it is to be understood that numerous changes and modifications may be made therein without departing from the scope, spirit and intent of the invention as set forth in the appended claims.

What I claim is:

1. A method of treating a human being for reducing or eliminating pain and discomfort caused by illness, or for relieving symptoms associated with a disorder, comprising:

(a) causing a patient to clench his hands tightly;

(b) extending the arms of the patient forwardly of the patient's body while said step (a) is being performed;

(c) said step (b) comprising positioning the forearms of the patient in close juxtaposition to the patient's chest in order to form a triangular arrangement, such that the two forearms form two legs of said triangular arrangement, and pushing each forearm toward the other until pressure is felt by the patient at the clenched hands and sternum;

(d) said step (b) further comprising elevating the forearms to a position approximately level with and in front of the sternum of the patient; and (e) externally applying pressure along muscles of the forearms of the patient;

said step (e) comprising positioning a thumb of a hand interiorly for applying localized pressure thereby on the anterior extensor digitorum muscle area closest to the respective wrist, while the forefinger of each hand applies considerable localized pressure against the posterior extensor carpi ulnaris muscle area; and, thereafter, gradually moving each hand upwardly along the forearms, toward the elbow, during which pressure is applied to the posterior extensor carpi ulnaris muscle area of each respective forearm via a respective forefinger, and applying pressure to the anterior brachioradialis muscle area of each respective forearm by a respective thumb, starting with the extensor carpi radialis bravis muscle area and up to the extensor carpi radialis longus at the elbow; and at each elbow, on the anterior side thereof, applying pressure to the flexor carpi ulnaris muscles by means of a respective forefinger, and, also, upon reaching the elbow, applying concentrated pressure via a respective forefinger to the ulna coronoid process bones, and, also, applying pressure to the olecranon process bone of the ulna; and simultaneously with the application of pressure to the ulna bones, applying pressure by means of the respective thumbs to the remainder of the upper anterior brachioradialis muscles and the upper part of the extensor carpi radialis brevis;

step (c) being carried out during the entire time that said step (e) is being performed.

2. The method of treating a human being for reducing or eliminating pain and discomfort caused by illness according to claim 1, wherein said step (a) comprises clenching the hands such that the left and right thumbs are crossed over each other, and the fingers of the left and right hands are crossed at right angles.

* * * * *